US006887989B2

(12) United States Patent
Simard et al.

(10) Patent No.: US 6,887,989 B2
(45) Date of Patent: May 3, 2005

(54) **SEQUENCES FROM *PISCIRICKETTSIA SALMONIS***

(75) Inventors: Nathalie Simard, Fredericton (CA); Huub Brouwers, Charlottetown (CA); Simon Jones, Vancouver (CA); Steve Griffiths, Fredericton (CA); Pablo Valenzuela, Santiago (CL); Luis Burzio, Santiago (CL)

(73) Assignee: Novartis AG, Basel (CH)

( * ) Notice: Subject to any disclaimer, the term of this patent is extended or adjusted under 35 U.S.C. 154(b) by 43 days.

(21) Appl. No.: 10/241,602

(22) Filed: Sep. 11, 2002

(65) Prior Publication Data

US 2003/0138446 A1 Jul. 24, 2003

Related U.S. Application Data

(63) Continuation-in-part of application No. PCT/GB01/01055, filed on Mar. 12, 2001.

(30) Foreign Application Priority Data

| | | |
|---|---|---|
| Mar. 11, 2000 | (GB) | 0005838 |
| Jul. 1, 2000 | (GB) | 0016080 |
| Jul. 1, 2000 | (GB) | 0016082 |
| Jul. 29, 2000 | (GB) | 0018599 |

(51) Int. Cl.[7] .......... C07H 21/04

(52) U.S. Cl. .......... 536/23.7; 536/24.32; 536/22.1; 435/320.1; 435/975; 435/6

(58) Field of Search .......... 536/23.7, 24.32, 536/22.1; 435/975, 320.1, 6

(56) References Cited

U.S. PATENT DOCUMENTS

2003/0165526 A1 9/2003 Kuzyk et al.

FOREIGN PATENT DOCUMENTS

| | | |
|---|---|---|
| CA | 2381708 | 4/2002 |
| GB | 2 356 632 | 5/2001 |

OTHER PUBLICATIONS

Henriquez et al. Gencore Accession No. AY256822. Aug. 27, 2001.*
Tosco et al. Gencore Accession No. AJ43594. Jul. 12, 1999.*
Barnes et al., "Purification of *Piscirickettsia salmonis* and partial characterization of antigens", Diseases of Aquatic Organisms, vol. 33(1) , pp. 33–41, (1998).
Jones et al., "Virulence and antigenic characteristics of a cultured Rickettsiales–like organism isolated from farmed Atlantic salmon Salmo salar in eastern Canada", Disease of Aquatic Organisms, vol. 33(1), pp. 25–31, (1998).
Kuzyk et al., "OspA, a Lipoprotein Antigen of the Obligate Intracellular Bacterial Pathogen *Piscirickettsia salmonis*", J. Mol. Microbiol. Biotechnol., vol. 3(1), pp. 83–93, (2001).
Marshall et al., "Minimally Invasive Detection of *Piscirickettsia salmonis* in Cultivated Salmonids via the PCR", Applied and Environmental Microbiology, vol. 64(8), pp. 3066–3069, (Aug. 1998).
Goh et al., "HSP60 Gene Sequences as Universal Targets for Microbial Species Identification: Studies with Coagulase–Negative Staphylococci", J. Clin. Microbiol., vol. 34, No. 4, pp. 818–823, (Apr. 1996).
Kohler et al., "Continuous cultures of fused cells secreting antibody of predefined specificity", Nature, vol. 256, pp. 495–497, (Aug. 7, 1975).
Smith et al., "Single–step purification of polypeptides expressed in *Escherichia coli* as fusions with glutathione S–transferase", Gene, vol. 67, pp. 31–40, (1988).
Triglia et al., "A procedure for in vitro amplification of DNA segments that lie outside the boundries of known sequences", Nucl. Acids Res., vol. 16, No. 16, pp. 8186, (1988).
Henriquez et al. GenBank Deposit Accession No. AY256822, dated May 12, 2003.
Kuzyk et al., *J. Mol. Microbiol. Biotechno.* 3(1):83–93, 2001.
Kuzyk et al., *Vaccine* 19:2337–2344, 2001.
Genbank Accession No. AF184152, submitted Sep. 10, 1999.
Millennium Second World Congress on Vaccines and Immunizations, Liége, Belgium, Aug. 29, 2000 through Sep. 3, 2000, see Workshop 11, p. 22.
U.S. patent application Publication No. U.S. 2003/0147909 A1, publication date: Aug. 7, 2003, Sergio Herman Marshall Gonzalez, "Highly Immunogenic Protein Against the Intracelluar Pathogen . . . ".

* cited by examiner

*Primary Examiner*—Jennifer E. Graser
(74) *Attorney, Agent, or Firm*—David L. Marks

(57) ABSTRACT

The present invention relates to a fish vaccine. More specifically the invention relates to a vaccine to protect salmon against infection by *Piscirickettsia salmonis*. The invention is based on or derived from the nucleic acid or amino acid sequence of antigens from *Piscirickettsia salmonis*. Nucleic acid and/or amino acid sequences may be used in the preparation of a vaccine to protect against infection by *Piscirickettsia salmonis.*

8 Claims, No Drawings

SEQUENCE LISTING

<160> NUMBER OF SEQ ID NOS: 34

<210> SEQ ID NO 1
<211> LENGTH: 404
<212> TYPE: DNA
<213> ORGANISM: Piscirickettsia salmonis

<400> SEQUENCE: 1
tgagtggcga ggagataagc taaaatgagt caagcattag ttgaatttaa aacggtagat 60
catgtgctgc aagccttagg cgttgaaggg atgagtgcag cggatgtgca tggcctgctg 120
attggtatgt tggcgagtca aagtaattta acctgtaaat catggttaga aaaagcgata 180
tttatgggag ctcaccttga tgctgaaagt gatcttttta gtaatatcat ggccaaagag 240
cagttaaagc agttagaggc attgtttaaa gtaagttggg agcagctctc tgcgggtgat 300
tttacttttg ctctgctgtt acctgatggt aatgctgcgt taactgagcg tgcgagttta 360
ttatgtgcct ggactcaagg ctttttaact ggcttgcatt tatc 404

<210> SEQ ID NO 2
<211> LENGTH: 126
<212> TYPE: PRT
<213> ORGANISM: Piscirickettsia salmonis

<400> SEQUENCE: 2

Met Ser Gln Ala Leu Val Glu Phe Lys Thr Val Asp His Val Leu Gln
1 5 10 15

Ala Leu Gly Val Glu Gly Met Ser Ala Ala Asp Val His Gly Leu Leu
20 25 30

Ile Gly Met Leu Ala Ser Gln Ser Asn Leu Thr Cys Lys Ser Trp Leu
35 40 45

Glu Lys Ala Ile Phe Met Gly Ala His Leu Asp Ala Glu Ser Asp Leu
50 55 60

Phe Ser Asn Ile Met Ala Lys Glu Gln Leu Lys Gln Leu Glu Ala Leu
65 70 75 80

Phe Lys Val Ser Trp Glu Gln Leu Ser Ala Gly Asp Phe Thr Phe Ala
85 90 95

Leu Leu Leu Pro Asp Gly Asn Ala Ala Leu Thr Glu Arg Ala Ser Leu
100 105 110

Leu Cys Ala Trp Thr Gln Gly Phe Leu Thr Gly Leu His Leu
115 120 125

<210> SEQ ID NO 3
<211> LENGTH: 591
<212> TYPE: DNA
<213> ORGANISM: Piscirickettsia salmonis

<400> SEQUENCE: 3
atgagtcaag cattagttga atttaaaacg gtagatcatg tgctgcaagc cttaggcgtt 60
gaagggatga gtgcagcgga tgtgcatggc ctgctgattg gtatgttggc gagtcaaagt 120
aatttaacct gtaaatcatg gttagaaaaa gcgatattta tgggagctca ccttgatgct 180
gaaagtgatc tttttagtaa tatcatggcc aaagagcagt taaagcagtt agaggcattg 240
tttaaagtaa gttgggagca gctctctgcg ggtgatttta cttttgctct gctgttacct 300
gatggtaatg ctgcgttaac tgagcgtgcg agtttattat gtgcctggac tcaaggcttt 360
ttaactggct tgcatttatc gggtgttaat attgctaaat ataaagaagg tgaattagcg 420

-continued

```
acgaccttaa aagatttagc tgaagttgcg cagttggatt tagccattga agacagtaat    480

gaaaatgaag cggcatatac tgagattgct gaatatgtac gtatggcggc gctttttgtt    540

catagtgaat tagccggttc tggtcaagcg actcagatga ctgttcatta a             591


<210> SEQ ID NO 4
<211> LENGTH: 196
<212> TYPE: PRT
<213> ORGANISM: Piscirickettsia salmonis

<400> SEQUENCE: 4

Met Ser Gln Ala Leu Val Glu Phe Lys Thr Val Asp His Val Leu Gln
 1               5                  10                  15

Ala Leu Gly Val Glu Gly Met Ser Ala Ala Asp Val His Gly Leu Leu
            20                  25                  30

Ile Gly Met Leu Ala Ser Gln Ser Asn Leu Thr Cys Lys Ser Trp Leu
        35                  40                  45

Glu Lys Ala Ile Phe Met Gly Ala His Leu Asp Ala Glu Ser Asp Leu
    50                  55                  60

Phe Ser Asn Ile Met Ala Lys Glu Gln Leu Lys Gln Leu Glu Ala Leu
65                  70                  75                  80

Phe Lys Val Ser Trp Glu Gln Leu Ser Ala Gly Asp Phe Thr Phe Ala
                85                  90                  95

Leu Leu Leu Pro Asp Gly Asn Ala Ala Leu Thr Glu Arg Ala Ser Leu
            100                 105                 110

Leu Cys Ala Trp Thr Gln Gly Phe Leu Thr Gly Leu His Leu Ser Gly
        115                 120                 125

Val Asn Ile Ala Lys Tyr Lys Glu Gly Glu Leu Ala Thr Thr Leu Lys
    130                 135                 140

Asp Leu Ala Glu Val Ala Gln Leu Asp Leu Ala Ile Glu Asp Ser Asn
145                 150                 155                 160

Glu Asn Glu Ala Ala Tyr Thr Glu Ile Ala Glu Tyr Val Arg Met Ala
                165                 170                 175

Ala Leu Phe Val His Ser Glu Leu Ala Gly Ser Gly Gln Ala Thr Gln
            180                 185                 190

Met Thr Val His
        195


<210> SEQ ID NO 5
<211> LENGTH: 489
<212> TYPE: DNA
<213> ORGANISM: Piscirickettsia salmonis

<400> SEQUENCE: 5

atgaacagag gatgtttgca aggtagtagt ctaattatta tcagtgtgtt tttagttggc     60

tgtgcccaga actttagtcg tcaagaagtc ggagctgcga ctggggctgt tgttggcggt    120

gttgctggcc agctgtttgg taaaggtagt ggtcgagttg caatggccat tggtggtgct    180

gttttgggtg gattaattgg ttctaaaatc ggtcaatcga tggatcagca ggataaaata    240

aagctaaacc agagtttgga aaaggtaaaa gcagggcaag tgacacgttg gcgtaatcca    300

gatacaggca atagttatag tgttgagcca gtgcgtactt accagcgtta caataagcaa    360

gagcgtcgcc agcaatattg tcgagaattt cagcaaaagg cgatgattgc agggcagaag    420

caagagattt acggcactgc atgccggcaa ccggatggtc gttggcaagt catttcaaca    480

gaaaaataa                                                            489
```

-continued

<210> SEQ ID NO 6
<211> LENGTH: 162
<212> TYPE: PRT
<213> ORGANISM: Piscirickettsia salmonis

<400> SEQUENCE: 6

```
Met Asn Arg Gly Cys Leu Gln Gly Ser Ser Leu Ile Ile Ile Ser Val
 1               5                  10                  15

Phe Leu Val Gly Cys Ala Gln Asn Phe Ser Arg Gln Glu Val Gly Ala
            20                  25                  30

Ala Thr Gly Ala Val Val Gly Gly Val Ala Gly Gln Leu Phe Gly Lys
        35                  40                  45

Gly Ser Gly Arg Val Ala Met Ala Ile Gly Gly Ala Val Leu Gly Gly
    50                  55                  60

Leu Ile Gly Ser Lys Ile Gly Gln Ser Met Asp Gln Gln Asp Lys Ile
65                  70                  75                  80

Lys Leu Asn Gln Ser Leu Glu Lys Val Lys Ala Gly Gln Val Thr Arg
                85                  90                  95

Trp Arg Asn Pro Asp Thr Gly Asn Ser Tyr Ser Val Glu Pro Val Arg
            100                 105                 110

Thr Tyr Gln Arg Tyr Asn Lys Gln Glu Arg Arg Gln Gln Tyr Cys Arg
        115                 120                 125

Glu Phe Gln Gln Lys Ala Met Ile Ala Gly Gln Lys Gln Glu Ile Tyr
    130                 135                 140

Gly Thr Ala Cys Arg Gln Pro Asp Gly Arg Trp Gln Val Ile Ser Thr
145                 150                 155                 160

Glu Lys
```

<210> SEQ ID NO 7
<211> LENGTH: 1098
<212> TYPE: DNA
<213> ORGANISM: Piscirickettsia salmonis
<220> FEATURE:
<221> NAME/KEY: misc_feature
<222> LOCATION: 765, 1064
<223> OTHER INFORMATION: n = A,T,C or G

<400> SEQUENCE: 7

```
caaggaatat tggcaaaatg ggagaatgtt tctgctcaaa aagtgatggt tgccaaggtt      60

agtacagtta ataatgctgg agataatggt cagtcaggta aaaataataa tgaaaatatt     120

attgaaaaag caggtgctat tgtatttgcg gtactcgata cacagctaaa cagtgaccaa     180

cccgggactc cagtaatggc aacgattgtt caaggtaaat ttaaaaatgc caaattgttg     240

ggtagcttta aaagagagga tgaaaaacta gtcatttctt ttgatcgcat atctttgcct     300

gaacttgatc acagtatttc tattaaggcg tatgcaatta atgccacaac agcacaaaat     360

gcactgtctt cagatgtaga taatcattat ttattacgtt atggtgggct ctttgctgct     420

gcgtttttgc aaggctttgg cgattatttc tcccaaaact catcaagctt atgtggtggt     480

gcgacaacct gtattattac aggcactcaa tcaactgcag aacaaaatcg tacaacgaga     540

aaagccctat attctggttt aggtcaagtt ggaacaactt tagctggtaa agcaagcgct     600

gcatttgatc gccctccaac ggttacttta aatcaaggtg ttggtatggg gattttattt     660

atgtcggatg taaaggtgta agttaaaatg agtaataatc acacagataa aaattataat     720

tttgatgatg atcaagacat taatgaggat aaagaagacc ttgcngctag ataatgagcc     780
```

-continued

```
agcagttaaa agaaataatg cagatgctgt ttggcaaggg acttcactgt gggataaaat    840

aaggccgatg ttgcattatt atatcattgc tattattgca ttcgctgtag caggttatat    900

gatgtataac gcataccgaa ctttatatcc aaagcagtca gtgcagcagg ctgaggctaa    960

ccatttaagc tttagtaatc aggttgaaac tggcagtaag tcagcgaaag gcttttctcc   1020

cctggctcag tctcaagaaa ataaggtcaa aaataaaagt gggncttgga aaaaaagaag   1080

agataaaacc gaatgcta                                                 1098


<210> SEQ ID NO 8
<211> LENGTH: 226
<212> TYPE: PRT
<213> ORGANISM: Piscirickettsia salmonis

<400> SEQUENCE: 8

Gln Gly Ile Leu Ala Lys Trp Glu Asn Val Ser Ala Gln Lys Val Met
 1               5                  10                  15

Val Ala Lys Val Ser Thr Val Asn Asn Ala Gly Asp Asn Gly Gln Ser
            20                  25                  30

Gly Lys Asn Asn Asn Glu Asn Ile Ile Glu Lys Ala Gly Ala Ile Val
        35                  40                  45

Phe Ala Val Leu Asp Thr Gln Leu Asn Ser Asp Gln Pro Gly Thr Pro
    50                  55                  60

Val Met Ala Thr Ile Val Gln Gly Lys Phe Lys Asn Ala Lys Leu Leu
65                  70                  75                  80

Gly Ser Phe Lys Arg Glu Asp Glu Lys Leu Val Ile Ser Phe Asp Arg
                85                  90                  95

Ile Ser Leu Pro Glu Leu Asp His Ser Ile Ser Ile Lys Ala Tyr Ala
            100                 105                 110

Ile Asn Ala Thr Thr Ala Gln Asn Ala Leu Ser Ser Asp Val Asp Asn
        115                 120                 125

His Tyr Leu Leu Arg Tyr Gly Gly Leu Phe Ala Ala Ala Phe Leu Gln
    130                 135                 140

Gly Phe Gly Asp Tyr Phe Ser Gln Asn Ser Ser Ser Leu Cys Gly Gly
145                 150                 155                 160

Ala Thr Thr Cys Ile Ile Thr Gly Thr Gln Ser Thr Ala Glu Gln Asn
                165                 170                 175

Arg Thr Thr Arg Lys Ala Leu Tyr Ser Gly Leu Gly Gln Val Gly Thr
            180                 185                 190

Thr Leu Ala Gly Lys Ala Ser Ala Ala Phe Asp Arg Pro Pro Thr Val
        195                 200                 205

Thr Leu Asn Gln Gly Val Gly Met Gly Ile Leu Phe Met Ser Asp Val
    210                 215                 220

Lys Val
225


<210> SEQ ID NO 9
<211> LENGTH: 30
<212> TYPE: PRT
<213> ORGANISM: Piscirickettsia salmonis

<400> SEQUENCE: 9

Ala Asp Asn Gly Lys Leu Gln Leu Gln Ile Ser Gln Leu Lys Ala Gln
 1               5                  10                  15

Gln Thr Gln Leu Gln Gln Gln Val Ala Asn Leu Gln Gly Gln
            20                  25                  30
```

-continued

```
<210> SEQ ID NO 10
<211> LENGTH: 164
<212> TYPE: DNA
<213> ORGANISM: Piscirickettsia salmonis

<400> SEQUENCE: 10

gatctttaat ctcattaaaa tttatgtttc taatcgcgtg ggttattttc atcaaatacg     60

gcatttttag gaggagggat aacaacatca gcattaggtg agtggtttaa aacggaatcg    120

taaacatcat ggctatcgta ggctccgtct gcagtgaagc gatc                     164


<210> SEQ ID NO 11
<211> LENGTH: 44
<212> TYPE: PRT
<213> ORGANISM: Piscirickettsia salmonis

<400> SEQUENCE: 11

Asp Arg Phe Thr Ala Asp Gly Ala Tyr Asp Ser His Asp Val Tyr Asp
 1               5                  10                  15

Ser Val Leu Asn His Ser Pro Asn Ala Asp Val Val Ile Pro Pro Pro
            20                  25                  30

Lys Asn Ala Val Phe Asp Glu Asn Asn Pro Arg Asp
        35                  40


<210> SEQ ID NO 12
<211> LENGTH: 195
<212> TYPE: DNA
<213> ORGANISM: Piscirickettsia salmonis
<220> FEATURE:
<221> NAME/KEY: misc_feature
<222> LOCATION: 31, 41, 147
<223> OTHER INFORMATION: n = A,T,C or G

<400> SEQUENCE: 12

ataagcctag atgatgatat tgcgggaata nccattgatt nacaggcctt aagcgttttg     60

gccgtgacga tgtggcacca agaaaaatac aagatatcag caaagcgcag ctggcgtaaa    120

cttcatgtgg ccgttgatga tgatcantat attcaagccg cactcatcac cgatcgctat    180

gaagcagatg aggag                                                     195


<210> SEQ ID NO 13
<211> LENGTH: 65
<212> TYPE: PRT
<213> ORGANISM: Piscirickettsia salmonis
<220> FEATURE:
<221> NAME/KEY: VARIANT
<222> LOCATION: 11, 14, 49
<223> OTHER INFORMATION: Xaa = Any Amino Acid

<400> SEQUENCE: 13

Ile Ser Leu Asp Asp Asp Ile Ala Gly Ile Xaa Ile Asp Xaa Gln Ala
 1               5                  10                  15

Leu Ser Val Leu Ala Val Thr Met Trp His Gln Glu Lys Tyr Lys Ile
            20                  25                  30

Ser Ala Lys Arg Ser Trp Arg Lys Leu His Val Ala Val Asp Asp Asp
        35                  40                  45

Xaa Tyr Ile Gln Ala Ala Leu Ile Thr Asp Arg Tyr Glu Ala Asp Glu
    50                  55                  60

Glu
65
```

-continued

<210> SEQ ID NO 14
<211> LENGTH: 213
<212> TYPE: DNA
<213> ORGANISM: Piscirickettsia salmonis
<220> FEATURE:
<221> NAME/KEY: misc_feature
<222> LOCATION: 186
<223> OTHER INFORMATION: n = A,T,C or G

<400> SEQUENCE: 14

```
tatgagatta aagatcatgg tagaatgcac tggcaaaaga cacgacaata cggcaagcgt     60

aattattctg agttggcgat tcagcgttac aaacgcattt tgggcaacac gatgcagtcc    120

agagacatat cgcgacagaa aaatgaagga ctaattggcg cgggtatttt aaatagagat    180

gaccantctc ggcatgccgg tgacaataat gta                                 213
```

<210> SEQ ID NO 15
<211> LENGTH: 71
<212> TYPE: PRT
<213> ORGANISM: Piscirickettsia salmonis
<220> FEATURE:
<221> NAME/KEY: VARIANT
<222> LOCATION: 62
<223> OTHER INFORMATION: Xaa = Any Amino Acid

<400> SEQUENCE: 15

```
Tyr Glu Ile Lys Asp His Gly Arg Met His Trp Gln Lys Thr Arg Gln
 1               5                  10                  15

Tyr Gly Lys Arg Asn Tyr Ser Glu Leu Ala Ile Gln Arg Tyr Lys Arg
            20                  25                  30

Ile Leu Gly Asn Thr Met Gln Ser Arg Asp Ile Ser Arg Gln Lys Asn
        35                  40                  45

Glu Gly Leu Ile Gly Ala Gly Ile Leu Asn Arg Asp Asp Xaa Ser Arg
    50                  55                  60

His Ala Gly Asp Asn Asn Val
65                  70
```

<210> SEQ ID NO 16
<211> LENGTH: 115
<212> TYPE: DNA
<213> ORGANISM: Piscirickettsia salmonis
<220> FEATURE:
<221> NAME/KEY: misc_feature
<222> LOCATION: 7
<223> OTHER INFORMATION: n = A,T,C or G

<400> SEQUENCE: 16

```
gatcaangcc cgcatattaa tcgacgacca cgatattcaa aagttaaaaa ttcaaaatat     60

ccgccaacat attgcctatt tacctcagca tggtgactta tttaatggca cgatc         115
```

<210> SEQ ID NO 17
<211> LENGTH: 38
<212> TYPE: PRT
<213> ORGANISM: Piscirickettsia salmonis
<220> FEATURE:
<221> NAME/KEY: VARIANT
<222> LOCATION: 2
<223> OTHER INFORMATION: Xaa = Any Amino Acid

<400> SEQUENCE: 17

```
Ile Xaa Ala Arg Ile Leu Ile Asp Asp His Asp Ile Gln Lys Leu Lys
 1               5                  10                  15

Ile Gln Asn Ile Arg Gln His Ile Ala Tyr Leu Pro Gln His Gly Asp
            20                  25                  30
```

-continued

```
Leu Phe Asn Gly Thr Ile
        35


<210> SEQ ID NO 18
<211> LENGTH: 179
<212> TYPE: DNA
<213> ORGANISM: Piscirickettsia salmonis
<220> FEATURE:
<221> NAME/KEY: misc_feature
<222> LOCATION: 25, 141, 164, 167, 177
<223> OTHER INFORMATION: n = A,T,C or G

<400> SEQUENCE: 18

gcacgcatat cgatacctaa cgtcntttca agaacaaaaa tattataaac aagccataga     60

agtcagccaa ttacttggcc ttgactcaat tattgagcgc ttgcccaaag gctatcacac    120

tcctgttgcc aatcatgccg natattaatt gactacgcac gatnttncaa agcttantg     179


<210> SEQ ID NO 19
<211> LENGTH: 48
<212> TYPE: PRT
<213> ORGANISM: Piscirickettsia salmonis
<220> FEATURE:
<221> NAME/KEY: VARIANT
<222> LOCATION: 47
<223> OTHER INFORMATION: Xaa = Any Amino Acid

<400> SEQUENCE: 19

His Ala Tyr Arg Tyr Leu Thr Ser Phe Gln Glu Gln Lys Tyr Tyr Lys
 1               5                  10                  15

Gln Ala Ile Glu Val Ser Gln Leu Leu Gly Leu Asp Ser Ile Ile Glu
            20                  25                  30

Arg Leu Pro Lys Gly Tyr His Thr Pro Val Ala Asn His Ala Xaa Tyr
        35                  40                  45


<210> SEQ ID NO 20
<211> LENGTH: 390
<212> TYPE: DNA
<213> ORGANISM: Piscirickettsia salmonis
<220> FEATURE:
<221> NAME/KEY: misc_feature
<222> LOCATION: 55
<223> OTHER INFORMATION: n = A,T,C or G

<400> SEQUENCE: 20

ttattgagcg cttgcccaaa ggctatcaca ctcctgttgc caatcatgcc atggnagtcg     60

ctacctcgcg gtatcattca gcgcattgcg attgcccgtg ccctgattca taagccacca    120

atcgtcctat tcgatgaggc caatacggcc atggacatgc aaggtgatac catcttaatt    180

aatgtgcttg aacaacttaa aggcacctgc acactcatcc tcgtctctca tcgcccatca    240

ttgctggcac atgcagataa aatctttatc ctcgagaata aaaatctggt ggagaaagtc    300

acatgagctc tgcactaacc gcccaggagc ataatattcg cactgcgttt attaacagcc    360

tcgaaccact gttaactgca ttaggctggc                                     390


<210> SEQ ID NO 21
<211> LENGTH: 101
<212> TYPE: PRT
<213> ORGANISM: Piscirickettsia salmonis
<220> FEATURE:
<221> NAME/KEY: VARIANT
<222> LOCATION: 19
<223> OTHER INFORMATION: Xaa = Any Amino Acid
```

-continued

<400> SEQUENCE: 21

```
Leu Leu Ser Ala Cys Pro Lys Ala Ile Thr Leu Leu Leu Pro Ile Met
 1               5                  10                  15

Pro Trp Xaa Ser Leu Pro Arg Gly Ile Ile Gln Arg Ile Ala Ile Ala
            20                  25                  30

Arg Ala Leu Ile His Lys Pro Pro Ile Val Leu Phe Asp Glu Ala Asn
        35                  40                  45

Thr Ala Met Asp Met Gln Gly Asp Thr Ile Leu Ile Asn Val Leu Glu
    50                  55                  60

Gln Leu Lys Gly Thr Cys Thr Leu Ile Leu Val Ser His Arg Pro Ser
65                  70                  75                  80

Leu Leu Ala His Ala Asp Lys Ile Phe Ile Leu Glu Asn Lys Asn Leu
                85                  90                  95

Val Glu Lys Val Thr
            100
```

<210> SEQ ID NO 22
<211> LENGTH: 280
<212> TYPE: DNA
<213> ORGANISM: Piscirickettsia salmonis
<220> FEATURE:
<221> NAME/KEY: misc_feature
<222> LOCATION: 9, 38, 236, 255, 256, 273
<223> OTHER INFORMATION: n = A,T,C or G

<400> SEQUENCE: 22

```
ggttgttgnt ggaatatcaa ggctaatatt ggtaaatngc caattttcat catcttcatt      60

tgtgcttgta ttattatttt tatcataacg aaaattgaca tgttcaaagc aaatgtggcc     120

atcaatatgg gcgagttgct tttgcgtggg aacatactct ggagggagtt taaagacttc     180

ttgtacattt atcttcagca ctaccaatcg actgtaagcg gttccagacg gaggtngcac     240

gattaattgg ctgtnnacag cgccctgaca gtnacggtgc                           280
```

<210> SEQ ID NO 23
<211> LENGTH: 91
<212> TYPE: PRT
<213> ORGANISM: Piscirickettsia salmonis
<220> FEATURE:
<221> NAME/KEY: VARIANT
<222> LOCATION: 3, 9, 15, 81, 91
<223> OTHER INFORMATION: Xaa = Any Amino Acid

<400> SEQUENCE: 23

```
His Arg Xaa Cys Gln Gly Ala Val Xaa Ser Gln Leu Ile Val Xaa Pro
 1               5                  10                  15

Pro Ser Gly Thr Ala Tyr Ser Arg Leu Val Val Leu Lys Ile Asn Val
            20                  25                  30

Gln Glu Val Phe Lys Leu Pro Pro Glu Tyr Val Pro Thr Gln Lys Gln
        35                  40                  45

Leu Ala His Ile Asp Gly His Ile Cys Phe Glu His Val Asn Phe Arg
    50                  55                  60

Tyr Asp Lys Asn Asn Asn Thr Ser Thr Asn Glu Asp Asp Glu Asn Trp
65                  70                  75                  80

Xaa Phe Thr Asn Ile Ser Leu Asp Ile Pro Xaa
                85                  90
```

<210> SEQ ID NO 24
<211> LENGTH: 170
<212> TYPE: DNA

-continued

<213> ORGANISM: Piscirickettsia salmonis

<400> SEQUENCE: 24

```
ggatcatgct catcctctac gtcgatgcga tggtctcacc tttaggaacg gctttagcct     60

ataccggctc ttctacacgg atgctaacgg ccatgtctcg cgaaaaacag gttccgcgtt    120

tctttgacca tgtacacccc cactatggtg tttcccgtcg ttcattgatc               170
```

<210> SEQ ID NO 25
<211> LENGTH: 56
<212> TYPE: PRT
<213> ORGANISM: Piscirickettsia salmonis

<400> SEQUENCE: 25

```
Ile Met Leu Ile Leu Tyr Val Asp Ala Met Val Ser Pro Leu Gly Thr
 1               5                  10                  15

Ala Leu Ala Tyr Thr Gly Ser Ser Thr Arg Met Leu Thr Ala Met Ser
            20                  25                  30

Arg Glu Lys Gln Val Pro Arg Phe Phe Asp His Val His Pro His Tyr
        35                  40                  45

Gly Val Ser Arg Arg Ser Leu Ile
    50                  55
```

<210> SEQ ID NO 26
<211> LENGTH: 199
<212> TYPE: DNA
<213> ORGANISM: Piscirickettsia salmonis

<400> SEQUENCE: 26

```
gatgagcatg atcatatgca ggcctaatag accggctaac tgtaccatgg gtgcttgaaa     60

gtcaagctgg tgccagccat ttttaagcat acttggcggt agtgcaccaa taaatgacac    120

ttgacaagag caagtaaatc actaagcaga ttacaatcga gaggaccaga gagagcggga    180

tattgcgttt tgggtttga                                                 199
```

<210> SEQ ID NO 27
<211> LENGTH: 38
<212> TYPE: PRT
<213> ORGANISM: Piscirickettsia salmonis

<400> SEQUENCE: 27

```
Ser Asn Pro Lys Arg Asn Ile Pro Leu Ser Leu Val Leu Ser Ile Val
 1               5                  10                  15

Ile Cys Leu Val Ile Tyr Leu Leu Leu Ser Ser Val Ile Tyr Trp Cys
            20                  25                  30

Thr Thr Ala Lys Tyr Ala
        35
```

<210> SEQ ID NO 28
<211> LENGTH: 375
<212> TYPE: DNA
<213> ORGANISM: Piscirickettsia salmonis
<220> FEATURE:
<221> NAME/KEY: misc_feature
<222> LOCATION: 7
<223> OTHER INFORMATION: n = A,T,C or G

<400> SEQUENCE: 28

```
ggtaaangag tatcgatatt ggcgtttttt ggctgtattt tatggttcag gttgtgcgag     60

tacggtgcca acagggcgcc ttattctgat tatcctcatg tgtatgcatg cccgaataag    120
```

-continued

```
ttaagtactt tgtgttatcg tacagcgatt gcaccggttg gacactggtc tcagtataat    180

cagctgagct ttcagttgcc gattgctttg caagtaccat tgcgtcaagg acaattagag    240

ctacaagagt attatgctaa aaatcccgta ttgccttcat ctttgccttt atcaggccca    300

gcccgttaa cgtcttattt atatccattt ggattgtgtg caacaaaaat aattcgctta     360

gagagtttaa ctgat                                                     375


<210> SEQ ID NO 29
<211> LENGTH: 125
<212> TYPE: PRT
<213> ORGANISM: Piscirickettsia salmonis
<220> FEATURE:
<221> NAME/KEY: VARIANT
<222> LOCATION: 3
<223> OTHER INFORMATION: Xaa = Any Amino Acid

<400> SEQUENCE: 29

Gly Lys Xaa Val Ser Ile Leu Ala Phe Phe Gly Cys Ile Leu Trp Phe
 1               5                  10                  15

Arg Leu Cys Glu Tyr Gly Ala Asn Arg Ala Pro Tyr Ser Asp Tyr Pro
            20                  25                  30

His Val Tyr Ala Cys Pro Asn Lys Leu Ser Thr Leu Cys Tyr Arg Thr
        35                  40                  45

Ala Ile Ala Pro Val Gly His Trp Ser Gln Tyr Asn Gln Leu Ser Phe
    50                  55                  60

Gln Leu Pro Ile Ala Leu Gln Val Pro Leu Arg Gln Gly Gln Leu Glu
65                  70                  75                  80

Leu Gln Glu Tyr Tyr Ala Lys Asn Pro Val Leu Pro Ser Ser Leu Pro
                85                  90                  95

Leu Ser Gly Pro Gly Pro Leu Thr Ser Tyr Leu Tyr Pro Phe Gly Leu
            100                 105                 110

Cys Ala Thr Lys Ile Ile Arg Leu Glu Ser Leu Thr Asp
        115                 120                 125


<210> SEQ ID NO 30
<211> LENGTH: 627
<212> TYPE: PRT
<213> ORGANISM: Piscirickettsia salmonis

<400> SEQUENCE: 30

Met Ala Glu Ile Ile Gly Ile Asp Leu Gly Thr Thr Asn Ser Cys Val
 1               5                  10                  15

Ala Val Leu Asp Gly Asp Lys Pro Arg Val Ile Glu Ser Ala Glu Gly
            20                  25                  30

Asp Arg Thr Thr Pro Ser Ile Val Ala Tyr Thr Asn Asp Gly Val Thr
        35                  40                  45

Val Gly Gln Pro Ala Lys Arg Gln Ala Val Thr Asn Pro Asn Asn Thr
    50                  55                  60

Leu Phe Ala Val Lys Arg Leu Ile Gly Arg Lys Ser Ser Asp Asp Thr
65                  70                  75                  80

Val Gln Arg Asp Ile Glu Arg Leu Pro Tyr Thr Ile Ala Ala Ala Asp
                85                  90                  95

Asn Gly Asp Ala Trp Ile Asp Val Asn Gly Glu Lys Leu Ala Pro Pro
            100                 105                 110

Gln Ile Ser Ala Gln Val Leu Ala Lys Met Lys Lys Thr Ala Glu Asp
        115                 120                 125

Tyr Leu Gly Glu Asp Val Lys Glu Ala Val Ile Thr Val Pro Ala Tyr
```

-continued

```
    130                 135                 140

Phe Asn Asp Ala Gln Arg Gln Ala Thr Lys Asp Ala Gly Arg Ile Ala
145                 150                 155                 160

Gly Leu Asp Val Lys Arg Ile Ile Asn Glu Pro Thr Ala Ala Ala Leu
                165                 170                 175

Ala Tyr Gly Met Asp Lys Lys Arg Gly Asp Gly Val Ile Ala Val Tyr
            180                 185                 190

Asp Leu Gly Gly Gly Thr Phe Asp Ile Ser Ile Ile Glu Ile Ala Glu
        195                 200                 205

Val Asp Gly Glu His Gln Phe Glu Val Leu Ala Thr Asn Gly Asp His
    210                 215                 220

Thr Leu Gly Gly Glu Asp Phe Asp Leu Arg Leu Ile Ser Tyr Leu Val
225                 230                 235                 240

Asp Glu Phe Lys Lys Glu Gln Gly Ile Asp Glu Ala Ser Glu Lys Ala
                245                 250                 255

Lys Ile Glu Leu Ser Ser Thr Gln Gln Thr Asp Val Asn Leu Pro Tyr
            260                 265                 270

Ile Thr Ala Asp Ala Thr Gly Pro Lys His Met Asn Ile Arg Val Thr
        275                 280                 285

Arg Ala Lys Phe Glu Ser Leu Val Glu Asp Leu Val Glu Gly Thr Ile
    290                 295                 300

Glu Pro Cys Arg Val Ala Leu Lys Asp Ala Gly Leu Ser Val Asn Asp
305                 310                 315                 320

Val Thr Asp Val Ile Leu Val Gly Gly Gln Thr Arg Met Pro Lys Ala
                325                 330                 335

Gln Ala Val Val Lys Asn Phe Phe Gly Lys Glu Pro Arg Arg Asp Val
            340                 345                 350

Asn Pro Asp Glu Ala Val Ala Val Gly Ala Ala Ile Gln Gly Gly Val
        355                 360                 365

Leu Ala Gly Asp Val Lys Asp Val Met Leu Leu Asp Val Thr Pro Leu
    370                 375                 380

Ser Leu Gly Ile Glu Thr Met Gly Gly Val Met Thr Lys Leu Ile Glu
385                 390                 395                 400

Lys Asn Thr Thr Ile Pro Thr Lys Ser Gln Thr Phe Ser Thr Ala Gln
                405                 410                 415

Asp Asn Gln Asn Ala Val Thr Val His Val Leu Gln Gly Glu Arg Glu
            420                 425                 430

Val Ala Thr Gly Lys Lys Leu Thr Gly Arg Phe Asp Leu Ala Asp Ile
        435                 440                 445

Pro Pro Ala Pro Arg Gly Met Pro Leu Ile Leu Arg Val His Phe Asp
    450                 455                 460

Ile Asp Ala Asn Gly Thr Leu Asn Val Ser Ala Lys Asp Lys Gly Thr
465                 470                 475                 480

Gly Lys Glu Gln Ser Ile Val Ile Arg Arg Ser Ser Gly Leu Ser Asp
                485                 490                 495

Asp Glu Val Asp Ala Met Ile Lys Asp Ala Glu Asp His Ala Asp Asp
            500                 505                 510

Asp Lys Lys Phe Gln Glu Leu Val Gly Ala Arg Asn Asn Ala Glu Ala
        515                 520                 525

Met Ile His Ala Thr Glu Lys Gly Leu Lys Glu Ala Asp Gly Lys Val
    530                 535                 540

Ala Ala Asp Asp Lys Thr Ala Ile Glu Lys Ala Ile Ser Glu Leu Lys
545                 550                 555                 560
```

```
Asp Val Val Ser Gly Leu Asp Lys Ala Val Ile Asp Glu Lys Val Glu
                565                 570                 575

Ala Leu Thr Gln Ala Ser Ala Lys Met Ala Glu Val Leu Tyr Ala Asn
            580                 585                 590

Gln Gly Ala Glu Ala Glu Ala Ala Ala Ala Gly Ala Glu Gln Ala Gln
        595                 600                 605

Ser Gln Thr Asp Glu Lys Lys Asp Asp Asp Val Val Asp Ala Glu Phe
    610                 615                 620

Glu Glu Val
625


<210> SEQ ID NO 31
<211> LENGTH: 640
<212> TYPE: PRT
<213> ORGANISM: Piscirickettsia salmonis

<400> SEQUENCE: 31

Met Ala Glu Ile Ile Gly Ile Asp Leu Gly Thr Thr Asn Ser Cys Val
 1               5                  10                  15

Ala Val Leu Asp Gly Asp Lys Pro Arg Val Ile Glu Ser Ala Glu Gly
            20                  25                  30

Asp Arg Thr Thr Pro Ser Ile Val Ala Tyr Thr Asn Asp Gly Val Thr
        35                  40                  45

Val Gly Gln Pro Ala Lys Arg Gln Ala Val Thr Asn Pro Asn Asn Thr
    50                  55                  60

Leu Phe Ala Val Lys Arg Leu Ile Gly Arg Lys Ser Ser Asp Asp Thr
65                  70                  75                  80

Val Gln Arg Asp Ile Glu Arg Leu Pro Tyr Thr Ile Ala Ala Ala Asp
                85                  90                  95

Asn Gly Asp Ala Trp Ile Asp Val Asn Gly Glu Lys Leu Ala Pro Pro
            100                 105                 110

Gln Ile Ser Ala Gln Val Leu Ala Lys Met Lys Lys Thr Ala Glu Asp
        115                 120                 125

Tyr Leu Gly Glu Asp Val Lys Glu Ala Val Ile Thr Val Pro Ala Tyr
    130                 135                 140

Phe Asn Asp Ala Gln Arg Gln Ala Thr Lys Asp Ala Gly Arg Ile Ala
145                 150                 155                 160

Gly Leu Asp Val Lys Arg Ile Ile Asn Glu Pro Thr Ala Ala Ala Leu
                165                 170                 175

Ala Tyr Gly Met Asp Lys Lys Arg Gly Asp Gly Val Ile Ala Val Tyr
            180                 185                 190

Asp Leu Gly Gly Gly Thr Phe Asp Ile Ser Ile Ile Glu Ile Ala Glu
        195                 200                 205

Val Asp Gly Glu His Gln Phe Glu Val Leu Ala Thr Asn Gly Asp Thr
    210                 215                 220

His Leu Gly Gly Glu Asp Phe Asp Leu Arg Leu Ile Ser Tyr Leu Val
225                 230                 235                 240

Asp Glu Phe Lys Lys Glu Gln Gly Ile Asp Leu Asn Asn Asp Pro Leu
                245                 250                 255

Ala Leu Gln Arg Leu Lys Glu Ala Ser Glu Lys Ala Lys Ile Glu Leu
            260                 265                 270

Ser Ser Thr Gln Gln Thr Asp Val Asn Leu Pro Tyr Ile Thr Ala Asp
        275                 280                 285

Ala Thr Gly Pro Lys His Met Asn Ile Arg Val Thr Arg Ala Lys Phe
```

-continued

```
    290                 295                 300

Glu Ser Leu Val Glu Asp Leu Val Glu Gly Thr Ile Glu Pro Cys Arg
305                 310                 315                 320

Val Ala Leu Lys Asp Ala Gly Leu Ser Val Asn Asp Val Thr Asp Val
                325                 330                 335

Ile Leu Val Gly Gly Gln Thr Arg Met Pro Lys Ala Gln Ala Val Val
            340                 345                 350

Lys Asn Phe Phe Gly Lys Glu Pro Arg Arg Asp Val Asn Pro Asp Glu
        355                 360                 365

Ala Val Ala Val Gly Ala Ala Ile Gln Gly Gly Val Leu Ala Gly Asp
    370                 375                 380

Val Lys Asp Val Leu Leu Leu Asp Val Thr Pro Leu Ser Leu Gly Ile
385                 390                 395                 400

Glu Thr Met Gly Gly Val Met Thr Lys Leu Ile Glu Lys Asn Thr Thr
                405                 410                 415

Ile Pro Thr Lys Ala Ser Gln Thr Phe Ser Thr Ala Gln Asp Asn Gln
            420                 425                 430

Thr Ala Val Thr Val His Val Leu Gln Gly Glu Arg Glu Val Ala Thr
        435                 440                 445

Gly Asn Lys Ser Leu Gly Arg Phe Asp Leu Ala Asp Ile Pro Pro Ala
    450                 455                 460

Pro Arg Gly Met Pro Gln Val Glu Val Thr Phe Asp Ile Asp Ala Asn
465                 470                 475                 480

Gly Ile Leu Asn Val Ser Ala Lys Asp Lys Gly Thr Gly Lys Glu Gln
                485                 490                 495

Ser Ile Val Ile Arg Ala Ser Ser Gly Leu Ser Asp Asp Glu Val Asp
            500                 505                 510

Ala Met Ile Lys Asp Ala Glu Asp His Ala Asp Asp Asp Lys Lys Phe
        515                 520                 525

Gln Glu Leu Val Gly Ala Arg Asn Asn Ala Glu Ala Met Ile His Ala
    530                 535                 540

Thr Glu Lys Gly Leu Lys Glu Ala Gly Asp Lys Val Ala Ala Asp Asp
545                 550                 555                 560

Lys Thr Ala Ile Glu Lys Ala Ile Ser Glu Leu Lys Asp Val Val Ser
                565                 570                 575

Gly Asn Asp Lys Ala Val Ile Asp Glu Lys Val Glu Ala Leu Thr Gln
            580                 585                 590

Ala Ser Ala Lys Met Ala Glu Val Leu Tyr Ala Asn Gln Gly Ala Glu
        595                 600                 605

Ala Glu Ala Ala Ala Ala Ala Gly Ala Glu Gln Ala Gln Ser Gln Thr
    610                 615                 620

Asp Glu Lys Lys Asp Asp Asp Val Val Asp Ala Glu Phe Glu Glu Val
625                 630                 635                 640


<210> SEQ ID NO 32
<211> LENGTH: 1920
<212> TYPE: DNA
<213> ORGANISM: Piscirickettsia salmonis

<400> SEQUENCE: 32

atggctgaaa ttattggtat tgatttggga acaaccaact cttgtgttgc tgttcttgat      60

ggtgataaac cgcgtgtgat tgagagtgca gaaggtgatc gtacgacacc ctctattgtc     120

gcttatacca atgatggggt tacagtcggt caaccggcta aacgtcaagc ggtgaccaat     180
```

-continued

```
ccaaataata ccctgtttgc agtcaaacgt ttaattggcc gtaagtcttc tgatgatacg    240
gtacagcgtg atatcgagcg ccttccctat acaattgctg cagcggataa cggtgatgct    300
tggattgatg taaatggtga aaaactagca ccaccacaaa tttctgcaca agtactcgca    360
aagatgaaaa aaacagccga agattatttg ggtgaagacg ttaaagaagc ggtgattaca    420
gttcctgctt attttaatga tgcgcaacgt caagcgacga aagatgcggg gcgtattgct    480
ggtttagatg tcaagcgcat tatcaatgag ccaacagccg ccgcactggc gtatggtatg    540
gataaaaagc gtggtgatgg tgttattgct gtgtatgact taggtggcgg tacttttgat    600
atttctatta ttgaaattgc tgaagtggat ggtgagcacc aatttgaagt tttagcgacc    660
aatggcgata cgcacttagg tggtgaagac tttgatttac gcttaatcag ttatttagtt    720
gatgagttta aaaaagagca aggtatagat ttaaataatg acccactggc attgcagcgc    780
ttgaaagaag cttctgaaaa agccaaaatc gagctgtctt caactcagca aacagatgtg    840
aacttgcctt atattacagc ggatgcaact ggccctaagc acatgaatat tcgcgtaaca    900
cgggctaaat ttgaatcatt agtagaagac ttggtagaag gaacgattga gccgtgtcgt    960
gtggcgctaa aagatgcggg tttatcagtg aatgatgtaa ccgatgtgat tttagtcggt   1020
ggtcaaacac ggatgccaaa agcacaagca gtcgttaaaa acttctttgg taaagagccg   1080
cgtcgtgatg tgaatccaga tgaagcggtt gcagtgggcg cagcaattca gggtggtgtg   1140
ctggccggtg atgttaaaga tgttttgtta ttagacgtta cgccattatc actcgggatt   1200
gagaccatgg gtggggtgat gacgaagttg attgagaaaa atacgacgat tccaacaaaa   1260
gcttcgcaaa ccttctcaac ggcgcaagat aatcaaactg cggtgactgt gcatgtgttg   1320
caaggtgagc gcgaagtggc gacaggcaat aaatcactgg gtcgttttga tttggccgat   1380
attccgccag caccacgtgg tatgccacaa gttgaggtga cttttgatat tgatgcgaac   1440
ggtattttaa atgtgtcggc taaagataaa ggcacgggta aagagcagtc gatcgttatt   1500
cgcgcctcta gtggcttatc ggatgacgaa gtggatgcga tgatcaaaga tgctgaagat   1560
catgctgatg atgataaaaa attccaagaa ctcgttggtg cgcgtaacaa tgctgaggcg   1620
atgattcatg cgactgaaaa aggcttaaaa gaagcaggtg acaaagtcgc tgctgatgat   1680
aaaacagcca ttgaaaaagc gattagtgag ctaaaagatg ttgtcagcgg taatgataaa   1740
gcagtgattg atgaaaaagt tgaagcatta acacaagctt cggcaaagat ggctgaagtg   1800
ctttatgcta atcagggggc tgaagctgag gcggcggcag cggctggagc ggagcaggct   1860
caatctcaaa cggatgagaa gaaagatgat gatgtcgttg atgctgagtt tgaagaagtt   1920
```

<210> SEQ ID NO 33
<211> LENGTH: 1662
<212> TYPE: DNA
<213> ORGANISM: Piscirickettsia salmonis

<400> SEQUENCE: 33

```
atgtcagcaa aagaagtgcg cttcggtacc ggttcccgtc aaaaaatgtt ggacggtgtt     60
aacctacttg caaatgcagt gaaagtcact ctaggtccac gcggacgcaa cgttatttta    120
gaaaagtcat ttggtgcccc aaccatcact aaagatggtg tatctgttgc caaagaaatc    180
gagcttagcg ataagttcga aaacatgggc gcacaaatgg tcaaagaagt cgcatctaaa    240
tcaaatgatg atgcaggtga cggtacgaca acggcgacag tattagcaca agcaattatt    300
caagaaggcg tgaagtctgt tgctgccggc atgaacccaa tggacctaaa acgcggcatc    360
gataaagcca ctattgctgc agttgctgca ttaaaagact tatctacacc gtgcacagac    420
```

-continued aacaaagcca ttgctcaagt cggtacaatt tcagcaaact ctgatgaaga aattggctct 480
atcattgcta aagcgatgga aaaagtatct accgacggcg taatcactgt tgaagaaggc 540
tctagccttg aaaacgaatt agatgttgtt gaagggatgc aattcgatcg cggttacctc 600
tctccatatt ttgtcaacaa acaagagaaa atgatcgctg aaatcgaaag cccatttatc 660
ttactcgtcg acaagaaaat ttctaacatt cgcgaattac tacccacatt agaatcagtt 720
gctaaatcag gcaagccatt attcatcatc gctgaagatg ttgaaggtga agctctggca 780
acactcgtcg ttaataacat tcgcggtatt gttaaagtgt gcgcagtaaa agcacctggc 840
tttggtgatc gtcgtaaagc gatgcttgaa gatattgcca tcttaactgg cggtactgta 900
atctctgaag aagttggcct agaccttgag aaagcaactc ttgagcactt aggtacagca 960
aaacgcatcg tcgtcactaa agacaataca accgttattg atggtgcggg tgaacaaact 1020
gcgatcgaag ctcgcgttac tcaaatccgt gcacaagttg aagaaacatc ctctgactac 1080
gaccgcgaga aactgcaaga gcgtgtcgct aagctatctg gtggtgttgc tgtcattaaa 1140
gatggcgcag cgactgaaat cgagatgaaa gagaagaaag accgcgttga tgatgcactg 1200
catgcaacac gcgccgcagt tgaagaaggt gtggttcctg gtggtggtgt tgcactggtt 1260
cgtgcaatgg ctgcagttaa agctcttgac ttcgcaaatg atgaacaagc ccaaggtgct 1320
aacatcttgt tgcgtgctat gagcgcacca ttacgtcaaa tcgttgagaa cgcaggtagc 1380
gaagcggctg taattcttga taaaattgtc aacggtgaag gtaactttgg ttataatgca 1440
gcaaccaatg agtttggtga tatgatcgaa atgggtattc ttgacccaac taaagtcaca 1500
cgttctgcac ttcaaaatgc agcttctatc gcaggtctta tgatcacaac agaagcgatg 1560
gttgcagagc ttcctaaaga agactcagca ggtggtgctg gcatgccgga tatgggaggc 1620
atgggcggta tgggtggtat gggtggtatg ggcatgatgt aa 1662

<210> SEQ ID NO 34
<211> LENGTH: 553
<212> TYPE: PRT
<213> ORGANISM: Piscirickettsia salmonis

<400> SEQUENCE: 34

Met Ser Ala Lys Glu Val Arg Phe Gly Thr Gly Ser Arg Gln Lys Met
1 5 10 15

Leu Asp Gly Val Asn Leu Leu Ala Asn Ala Val Lys Val Thr Leu Gly
20 25 30

Pro Arg Gly Arg Asn Val Ile Leu Glu Lys Ser Phe Gly Ala Pro Thr
35 40 45

Ile Thr Lys Asp Gly Val Ser Val Ala Lys Glu Ile Glu Leu Ser Asp
50 55 60

Lys Phe Glu Asn Met Gly Ala Gln Met Val Lys Glu Val Ala Ser Lys
65 70 75 80

Ser Asn Asp Asp Ala Gly Asp Gly Thr Thr Thr Ala Thr Val Leu Ala
85 90 95

Gln Ala Ile Ile Gln Glu Gly Val Lys Ser Val Ala Ala Gly Met Asn
100 105 110

Pro Met Asp Leu Lys Arg Gly Ile Asp Lys Ala Thr Ile Ala Ala Val
115 120 125

Ala Ala Leu Lys Asp Leu Ser Thr Pro Cys Thr Asp Asn Lys Ala Ile
130 135 140

Ala Gln Val Gly Thr Ile Ser Ala Asn Ser Asp Glu Glu Ile Gly Ser

-continued

```
145                 150                 155                 160

Ile Ile Ala Lys Ala Met Glu Lys Val Ser Thr Asp Gly Val Ile Thr
                165                 170                 175

Val Glu Glu Gly Ser Ser Leu Glu Asn Glu Leu Asp Val Val Glu Gly
            180                 185                 190

Met Gln Phe Asp Arg Gly Tyr Leu Ser Pro Tyr Phe Val Asn Lys Gln
        195                 200                 205

Glu Lys Met Ile Ala Glu Ile Glu Ser Pro Phe Ile Leu Leu Val Asp
    210                 215                 220

Lys Lys Ile Ser Asn Ile Arg Glu Leu Leu Pro Thr Leu Glu Ser Val
225                 230                 235                 240

Ala Lys Ser Gly Lys Pro Leu Phe Ile Ile Ala Glu Asp Val Glu Gly
                245                 250                 255

Glu Ala Leu Ala Thr Leu Val Val Asn Asn Ile Arg Gly Ile Val Lys
            260                 265                 270

Val Cys Ala Val Lys Ala Pro Gly Phe Gly Asp Arg Arg Lys Ala Met
        275                 280                 285

Leu Glu Asp Ile Ala Ile Leu Thr Gly Gly Thr Val Ile Ser Glu Glu
    290                 295                 300

Val Gly Leu Asp Leu Glu Lys Ala Thr Leu Glu His Leu Gly Thr Ala
305                 310                 315                 320

Lys Arg Ile Val Val Thr Lys Asp Asn Thr Thr Val Ile Asp Gly Ala
                325                 330                 335

Gly Glu Gln Thr Ala Ile Glu Ala Arg Val Thr Gln Ile Arg Ala Gln
            340                 345                 350

Val Glu Glu Thr Ser Ser Asp Tyr Asp Arg Glu Lys Leu Gln Glu Arg
        355                 360                 365

Val Ala Lys Leu Ser Gly Gly Val Ala Val Ile Lys Asp Gly Ala Ala
    370                 375                 380

Thr Glu Ile Glu Met Lys Glu Lys Lys Asp Arg Val Asp Asp Ala Leu
385                 390                 395                 400

His Ala Thr Arg Ala Ala Val Glu Glu Gly Val Val Pro Gly Gly Gly
                405                 410                 415

Val Ala Leu Val Arg Ala Met Ala Ala Val Lys Ala Leu Asp Phe Ala
            420                 425                 430

Asn Asp Glu Gln Ala Gln Gly Ala Asn Ile Leu Leu Arg Ala Met Ser
        435                 440                 445

Ala Pro Leu Arg Gln Ile Val Glu Asn Ala Gly Ser Glu Ala Ala Val
    450                 455                 460

Ile Leu Asp Lys Ile Val Asn Gly Glu Gly Asn Phe Gly Tyr Asn Ala
465                 470                 475                 480

Ala Thr Asn Glu Phe Gly Asp Met Ile Glu Met Gly Ile Leu Asp Pro
                485                 490                 495

Thr Lys Val Thr Arg Ser Ala Leu Gln Asn Ala Ala Ser Ile Ala Gly
            500                 505                 510

Leu Met Ile Thr Thr Glu Ala Met Val Ala Glu Leu Pro Lys Glu Asp
        515                 520                 525

Ser Ala Gly Gly Ala Gly Met Pro Asp Met Gly Gly Met Gly Gly Met
    530                 535                 540

Gly Gly Met Gly Gly Met Gly Met Met
545                 550
```

SEQUENCES FROM *PISCIRICKETTSIA SALMONIS*

This application is a continuation-in-part of International PCT Application No. PCTIGB 01/01055, file Mar. 12, 2001, which in its entirety is herein incorporated by reference.

FIELD OF THE INVENTION

The present invention relates to a fish vaccine. More specifically the invention relates to a vaccine to protect salmon against piscirickettsiosis, also referred to as salmonid rickettsial septicaemia (SRS).

BACKGROUND OF THE INVENTION

To date no commercially available vaccine has succeeded in controlling infections by *Piscirickettsia salmonis*, the causative agent of SRS. Accordingly there is a need for an effective vaccine against *Piscirickettsia salmonis*.

It is an object of the present invention to provide a protein based vaccine or a Nucleic Acid Vaccine (NAV) to protect fish against infection by *Piscirickettsia salmonis*, and thereby against SRS.

SUMMARY OF THE INVENTION

In one aspect of the invention, novel nucleic acid sequences from *Piscirickettsia salmonis* and their encoded amino acid sequences are provided.

In another aspect of the invention a method is provided for protecting fish against infection by *Piscirickettsia salmonis*, comprising administering to a fish one or more of the nucleic acid sequences and amino acid sequences of the invention.

A further aspect of the invention provides nucleic acid vaccines and protein vaccines comprising one or more of the nucleic acid sequences or amino acid sequences of the invention, for administration to fish to protect against SRS.

DETAILED DESCRIPTION OF THE INVENTION

The novel sequences of the genes of the invention and the encoded proteins are provided in SEQ ID NOS: 1 through 34 which are containing the Sequence Listing.

Psclone51A

A partial nucleotide seqyence of Psicone51A is contained in SEQ ID NO:1 and complete nucleotide sequence of Psclone51A are contained in SEQ ID NO:3. These sequences were obtained from a cDNA molecule from mRNA of*Piscirickettsia salmonis* type strain LF-89. (cat. no. VR-1361, ATCC, Manassas, Va.). The cloned material was sequenced in both directions from the 5' and 3' insertion sites using overlapping amplicons. PCR and RT-PCR comparing uninfected Chinook salmon embryonic (CHSE-214) cell lines and cell lines infected with *P. salmonis* confirmed that Psclone51A is specific to *P. salmonis* and is not derived from salmon host cells.

The amino acid sequence of the open reading frame (ORF) of the partial nucleotide sequence of Psclone51A is contained in SEQ ID NO:2. The amino acid sequence of the ORF of the complete nucleotide sequence of Psclone51A is contained in SEQ ID NO:4. Expression of the cloned sequence has yielded a protein of approximately 12 kDa.

The ORF of Psclone51A in SEQ ID NO: 3 does not have any significant homology at the nucleotide level with previous submissions to databases accessible by BLAST. At the protein level, a border line similarity with a hypothetical 21.5 kDa protein of *Escherichia coli* was found.

p10.6

An expression library was constructed from *Piscirickettsia salmonis* strain LF-89 cat. no. VR-1361, ATCC, Manasses, Va.), grown in CHSE-214 cells. An immunoreactive clone, (0110-2-5) (p10.6), was selected using homologous antisera from *Piscirickettsia salmonis* immunised rabbits and sequenced. The nucleotide sequence of 10.6 is in SEQ ID NO:5. The open reading frame (ORF) for the full gene was completed by inverse PCR from genomic *Piscirickettsia salmonis* DNA.

Polymerase chain reaction (PCR) primers were designed based on the sequence of clone p10.6. Using these primers, PCR and RT-PCR comparing uninfected Chinook salmon embryonic (CHSE-214) cell lines and cell lines infected with *P. salmonis* confirmed that clone p10.6 is specific to *P. salmonis* and is not derived from salmon host cells.

The amino acid sequence deduced for the open reading frame (ORF) is in SEQ ID NO:6. The ORF of p10.6 does not have any significant homology at the nucleotide level with previous submissions to databases accessible by BLAST. The derived amino acid sequence, but not the nucleotide sequence, shows significant homology to the 17 kDa antigen found in Rickettsia of the Spotted Fever Group, where it is considered a group specific, outer membrane protein.

IcmE

The nucleic acid sequence of IcmE is in SEQ ID NO:7). The genetic sequence has been derived from an inverse polymerase chain reaction (IPCR) product amplified from *Piscirickettsia salmonis* type strain LF-89 genomic DNA (gDNA). The IPCR product was sequenced in both direction from the 5' and 3' sides using overlapping amplicons.

The amino acid sequence deduced for the ORF is provided in SEQ ID NO:8. The protein encoded by the ORF of IcmE (403) has a 37% significant homology at the protein level to the IcmE protein of *Legionella pneumophila* when compared to previous submissions to databases accessible by BLAST.

p45

The amino acid sequence of a portion of the p45 major antigen of *P. salmonis* is provided in SEQ ID NO:9.

The amino acid sequence was derived from microsequencing of a protein approximately 45 kDa found to be immunoreactive to rabbit anti-*P salmonis* antibodies. Moreover, p45 was found uniquely in Chinook salmon embryonic (CHSE-214) cells infected with *Piscirickettsia salmonis* and not in uninfected CHSE-214 cells.

The amino acid sequence of p45 has no significant homology to other bacterial proteins when compared to previous submissions to databases accessible by BLAST.

The fragment of p45 provided in SEQ ID NO:9 can be used per se in preparation of an antigen-based vaccine. Alternatively, a nucleic acid sequence encoding this fragment can be employed in the context of a DNA vaccine against *P. salmonis*. The p45 sequence information can also be used to isolate and sequence genomic or cDNA clones from *P. salmonis* in order to enable production of a vaccine based on the complete nucleic acid sequence or amino acid sequence of p45.

clone 3

The following three plasmids have related nucleic acid sequences: clone3/original, clone3/3PST-R, and clone3/3APA-F. For clone3/original the nucleotide sequence is in SEQ ID NO:10 and the amino acid sequence encoded therein is in SEQ ID NO:11. For clone3/3PST-R the nucleotide sequence is found in SEQ ID NO:12 while the amino acid sequence encoded therein is in SEQ ID NO:13. For clone3/3APA-F the nucleotide sequence is in SEQ ID NO:14 while the amino acid sequence encoded therein is found in SEQ ID NO:15.

The proteins encoded by the ORF of clone3/original, clone3/3PST-R and clone3/3APA-F have respectively 40%, 38% and 34% significant homology at the protein level to different portion of the transposase protein of *Vibrio anguillarum* (NCBI Protein Database number AAA81776.1) when compared to previous submissions to databases accessible by BLAST.

clone 7

The following four plasmids have related nucleic acid sequences: clone7/original, clone7/XbaR, clone7/MunR, and clone 7/MunF. For clone7/original, the nucleotide sequence is contained in SEQ ID NO:16 and the amino acid sequence encoded thereby is in SEQ ID NO:17. For clone7/XbaR, the nucleotide sequence is contained in SEQ ID NO:18 and in amino acid sequence encoded thereby is in SEQ ID NO:19. For the clone7/MunR, the nucleotide sequence is contained in SEQ ID NO:20 and the amino acid sequence encoded thereby is in SEQ ID NO:21. For clone7/MunF, the nucleotide sequence is contained in SEQ ID NO:22 and the amino acid sequence encoded thereby is in SEQ ID NO:23.

The genetic sequences have been derived from an inverse polymerase chain reaction (IPCR) product amplified from *Piscirickettsia salmonis* genomic DNA (gDNA).

The peptides encoded by the ORF of clone7/original, clone7/XbaR, clone7/MunR, and clone 7/MunF have a 40% to 44% significant homology at the protein level to different portion of the ABC transporter ATP-binding protein of the other bacterial species when compared to previous submissions to databases accessible by BLAST.

There is sufficient reason to believe that the nucleotide and corresponding amino acid sequence are of *Piscirickettsia salmonis* origin. Also, part of the ORFs was found in an immuno-reactive clone of an expression library.

clone 20

Related nucleic acid sequences are clone20/original (SEQ ID NO:24), and clone20/20VSPF (SEQ ID NO: 26). The encoded amino acid sequences are SEQ ID NO:25 and SEQ ID NO: 27 respectively.

The genetic sequences have been derived from an inverse polymerase chain reaction (IPCR) product amplified from *Piscirickettsia salmonis* genomic DNA (gDNA).

The peptides encoded by the ORF of clone20/original, and clone20/20VSPF have a 41% and 51% significant homology at the protein level to an amino acid transporter/permase protein of other organisms when compared to previous submissions to databases accessible by BLAST.

clone 15

The nucleic acid sequence of clone15/original is contained in SEQ ID NO: 28 and the encoded amino acid sequence thereof is contained in SEQ ID NO: 29.

The nucleotide sequence and the peptide encoded by the ORF of clone15/original have no significant homology to proteins of other bacterial species when compared to previous submissions to databases accessible by BLAST.

From the previous information there is sufficient reason to believe that the nucleotide and corresponding amino acid sequence are of *Piscirickettsia salmonis* origin. Also, the ORF was found in an immuno-reactive clone of an expression library.

Hsp70

The amino acid sequence of Hsp70 is contained in SEQ ID NO: 30. The amino acid sequence obtained from another Hsp70 isolate (clone B) is contained in SEQ ID NO:31, and the nucleic acid sequence encoding that amino acid sequence is in SEQ ID NO:32.

The amino acid sequence of hsp70 has 70% significant homology at the protein level to *Coxiella burnetti* and *Legionella pneumophila* hsp70 proteins when compared to previous submissions to databases accessible by BLAST.

Hsp60

SEQ ID NO:33 contains the nucleic acid sequence of the hsp60 gene of *P. salmonis*. The amino acid sequence deduced from the nucleic acid sequence is contained in SEQ ID NO:34.

Characterization of the *P. salmonis* hsp60 gene was initiated by amplifying a 600 bp product from *P. salmonis* mRNA using universal degenerate primers. The primers are as described in Swee Han Goh et al.(1996) Journal Clin. Microbiol. 34(4): 818–823. The PCR product was sequenced by standard methods (Molecular Cloning: A Laboratory Manual (1989)$2^{nd}$ ed. Sambrook, J. et al., Cold Spring Harbor Laboratory, NY).

Once this first PCR product was sequenced, the sequence of the ORF was completed by performing several inverse PCR (IPCR) amplifications on genomic DNA from *Piscirickettsia salmonis* type strain LF-89 (Triglia et al, 1988, Nucl. Acids Res. 16: 8186). The IPCR products were sequenced in both directions from the 5' and 3' insertion sites using overlapping amplicons.

The nucleic acid sequence and protein sequence of *P. salmonis* hsp60 show similarity to the corresponding gene/protein in other species. The protein encoded by the ORF of *P. salmonis* hsp60 has a 75–77% significant homology to the GroEL protein of various Pseudomonas and Vibrio species when compared to previous submissions to databases accessible by BLAST.

Heat shock proteins are abundant molecules which participate in folding, assembly and disassembly of protein complexes. Hsp60 and Hsp70 are major targets of immune responses to a wide variety of pathogens, including bacteria, fungi, helminths and protozoan parasites. It has been demonstrated that immunization with certain pathogen hsps induces strong immune responses and provides protection against disease caused by these pathogens. The strength of these immune responses may reflect the abundance of these proteins, and their immunogenicity: multiple B cell and T cell epitopes are found on mycobacterial hsp60.

Consequently, there are grounds for believing that *P. salmonis* hsp70 and hsp60 can form the basis for a successful monovalent or multivalent vaccine targeted against SRS and related diseases.

The gene and protein sequences of the invention are preferably derived from *P. salmonis* type strain LF89. The invention encompasses nucleic acid sequences and amino acid sequences which are substantially homologous to the sequences provided in the Figures. "Substantially homologous" in this context means that a sequence, when compared to a reference sequence, has at least 60% homology, preferably at least 70% homology, more preferably at least 80% homology, more preferably at least 90% homology, and most preferably at least 95% homology to the reference sequence.

To determine the percent homology of two amino acid sequences or of two nucleic acid sequences, the sequences are aligned for optimal comparison purposes (e.g. gaps can be introduced in the sequence of a first amino acid or nucleic acid sequence for optimal alignment with a second amino acid or nucleic acid sequence and the intervening non-homologous sequence in the gap can be disregarded for comparison purposes). There is no requirement for the two sequences to be the same length. In general, the length of sequence across which the sequences are compared is the entire extent of the alignment. Optionally, the length of a reference sequence aligned for comparison purpose is at least 30%, preferably at least 40%, more preferably at least 50%, even more preferably at least 60%, and even more preferably at least, 70%, 80%, or 90% of the length of the reference sequence. It possible to restrict homology analysis to any particular portion of the reference sequence.

When a position in the first (reference) sequence is occupied by the same amino acid residue or nucleotide as the corresponding position in the sequence, the molecules are homologous at that position (i.e. there is identity at that position). In the case of nucleic acid sequence comparison there is also homology at a certain position where the codon triplet including the nucleotide encodes the same amino acid in both molecules being compared, due to degeneracy of the genetic code.

The percent homology between two sequences is a function of the number of homologous positions shared by the sequences (i.e., % homology=no. of homologous positions/total no. of positions). Optionally, the comparison of sequences and determination of percent homology can be accomplished using a mathematical algorithm. Suitable algorithms are incorporated in to the NBLAST and XBLAST programs of Altschul et al. (1990) J. Mol. Biol. 215:430–10.

The definition of homologous sequences provided above embraces fragments of the reference nucleic acid sequence or amino acid sequence. For present purposes a “fragment” of a protein of the invention is understood to mean any peptide molecule having at least 20, optionally at least 30, or at least 40 contiguous amino acids of the reference amino acid sequence. A “fragment” of a nucleic acid reference sequence is any part of that sequence comprising at least 50, optionally at least 75, or at least 100 consecutive nucleotides.

Also comprised within the nucleic acid sequences of the invention are sequences which hybridize to the reference nucleic acid sequences under stringent conditions. “Stringent” hybridization conditions in the sense of the present invention are defined as those described by Sambrook et al., Molecular Cloning, A Laboratory Manual, Cold Spring Harbor Laboratory Press (1989), 1.101–1.104, i.e. a positive hybridization signal is still observed after washing for 1 hour with lx SSC buffer and 0.1% SDS at 55° C., preferably at 62° C. and most preferably at 68° C., in particular for 1 hour in 0.2×SSC buffer and 0.1% SDS at 55° C., preferably at 62° C. and most preferably at 68° C.

In particular, the invention extends to oligonucleotides 15 to 100, preferably 20 to 50, most preferably 25 to 35 nucleotides in length, which are complementary to any of the nucleic acid sequences depicted in the figures or which are capable of hybridising to these sequences under stringent conditions.

The amino acid sequences of the invention also comprise synthetic analogues or derivatives of the sequences in the Figures, or of homologues of those sequences. A “derivative” of an amino acid sequence is a sequence related to the reference sequence either on the amino acid sequence level (e.g. a homologous sequence wherein certain naturally-occurring amino acids are replaced with synthetic amino acid substitutes) or at the 3D level, i.e. molecules having approximately the same shape and conformation as the reference amino acid sequence. Thus, derivatives include mutants, mimetics, mimotopes, analogues, monomeric forms and functional equivalents. Amino acid sequence derivatives retain the ability to induce the production of antibodies that recognize and (cross)-react with antigens of *P. salmonis* and/or to induce an immune response in fish that protects against infection with this pathogen.

The present invention provides the use of any of the nucleic acid sequences or amino acid sequences shown in the Figures, or related sequences, in the manufacture of a vaccine for the protection of fish against infection by *Piscirickettsia salmonis.*

The invention further provides a vaccine to protect fish against *Piscirickettsia salmonis* wherein the vaccine includes at least one nucleic acid or peptide sequence as defined herein, together with a pharmaceutically acceptable carrier.

A diagnostic test kit is also provided in accordance with the invention, whereby the kit may comprise a nucleic acid sequence or amino acid sequence of the invention, or may comprise an antibody capable of recognising any of the amino acid sequences of the invention.

The isolated nucleic acid sequences from *P. salmonis* can be exploited in the conventional manner, by cloning the gene into an expression vector for generation of large quantities of purified or isolated recombinant protein. A purified antigen can also be obtained by non-recombinant techniques, i.e. through extraction from cells by conventional purification methods. Alternatively, the protein or polypeptide can be synthesized chemically using standard peptide synthesis techniques. A vaccine comprising this purified or isolated recombinant or non-recombinant protein can be termed an antigen-based vaccine.

An “isolated” or “purified” protein is defined as being substantially free of cellular material or other contaminating proteins from the cell or tissue source from which the purified protein is derived, or substantially free from chemical precursors or other chemicals when chemically synthesized. The language “substantially free of cellular material” includes preparations of a candidate protein in which the protein is separated from cellular components of the cells from which it is isolated or recombinantly produced. In one embodiment, the language “substantially free of cellular material” includes preparations of candidate protein having less than about 30% (by dry weight) of non-candidate protein (also referred to herein as a “contaminating protein”), more preferably less than about 20% of contaminating protein, still more preferably less than about 10% of contaminating protein, and most preferably less than about 5% contaminating protein. When the candidate protein or biologically active portion thereof is recombinantly produced, it is also preferably substantially free of culture medium, i.e., culture medium represents less than about 20%, more preferably less than about 10%, and most preferably less than about 5% of the volume of the protein preparation.

Alternatively, the genes of the invention can be incorporated into Nucleic Acid Vaccines (NAVs), whereby the NAV is taken up by host cells of a living animal, and expression of the gene takes place within the cytosol.

A gene inserted into a DNA vector can be inoculated directly into a fish (e.g. orally, intramuscularly or intraperitoneally) for expression in vivo within fish cells. Thus, in one aspect of the invention there is provided a nucleic acid vaccine comprising a pharmaceutically acceptable carrier and a DNA plasmid in which a nucleic acid sequence encoding a

*P. salmonis* gene of the invention is operably linked to a transcriptional regulatory sequence. Transcriptional regulatory sequences include promoters, polyadenylation sequences and other nucleotide sequences such as the immune-stimulating oligonucleotides having unmethylated CpG dinucleotides, or nucleotide sequences that code for other antigenic proteins or adjuvanting cytokines. For optimal in vivo expression it may be preferred to select transcriptional regulatory sequences endogenous to the fish to be vaccinated. For instance, endogenous cytokine or actin gene promoters may be considered. The DNA can be present in naked form or it can be administered together with an agent facilitating cellular uptake (e.g. liposomes or cationic lipids). The technology of DNA vaccination of fish is explained in more detail in U.S. Pat. No. 5,780,448, which is incorporated herein by reference.

Another aspect of the invention pertains to vectors, preferably expression vectors, comprising a nucleic acid sequencing encoding a gene of the invention (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of directing the expression of genes to which they are operatively linked. Such vectors are referred to herein as "expression vectors". In general, expression vectors of utility in recombinant DNA techniques are often in the form of plasmids. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, operatively linked to the nucleic acid sequence to be expressed. Recombinant expression vectors of the invention may be used for expression within the intended recipient of the antigen of the invention (as a DNA vaccine) or for expression within a host organism other than the final recipient (for production of recombinant antigen vaccines).

Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

Another aspect of the invention pertains to host cells into which a recombinant expression vector of the invention has been introduced. The terms "host cell" and "recombinant host cell" are used interchangeably herein. A host cell can be any prokaryotic or eukaryotic cell. For example, hsp proteins can be expressed in bacterial cells such as *E. coli*, insect cells (using baculovirus expression vectors) yeast cells or mammalian cells. Other suitable host cells are known to those skilled in the art (e.g. Goeddel, Gene Expression Technology: Methods in Enzymology 185, Academic Press, San Diego, Calif. (1990)). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

The present invention also relates to a method of generating monoclonal or polyclonal antibodies to an amino acid sequence of the invention. In this embodiment, an effective amount of the amino acid sequence (i.e., an amount which results in an immune response in the host) is introduced into an animal host which results in production of antibodies to the substance in the host. The antibodies are removed from the host and purified using known techniques (e.g. chromatography), thereby resulting in production of polyclonal antibodies. Procedures for immunizing animals, eg. mice, with proteins and selection of hybridomas producing immunogen-specific monoclonal antibodies are well known in the art (see for example Kohler and Milstein (1975) Nature 256: 495–497). The antibodies of the invention recognize (have an affinity to) at least one of the amino acid sequences disclosed herein. Preferably, the antibodies of the invention are raised against an isolated or purified amino acid sequence of the invention.

The vaccines manufactured in accordance with the methodology of the invention are suited for administering to any aquatic animal species for preventative or therapeutic purposes. The vaccines of the invention can be employed in treatment of teleosts such as salmon (Chinook, Atlantic, Coho), trout (including rainbow trout), carp, sea bream, sea bass, yellowtail, tilapia, grouper, catfish, halibut, haddock, or optionally for treatment of other aquatic species such as crustaceans and mollusks. Salmonid fish are the preferred species for treatment.

It is possible to immunize a subject with the neutral or the salt forms of the present purified or isolated proteins, either administered alone or in admixture with a pharmaceutically acceptable vehicle or excipient. Typically, vaccines are prepared as liquid solutions or suspensions; solid forms suitable for solution in, or suspension in, liquid vehicles prior to administration may also be prepared. The preparation may be emulsified or the active ingredient encapsulated in liposome vehicles. The pharmaceutical compositions of the invention may be administered in a form for immediate release or by extended release.

Pharmaceutically acceptable carriers or vehicles include conventional excipients, and may be, for example, solvents such as water, oil or saline, dextrose, glycerol, wetting or emulsifying agents, bulking agents, coatings, binders, fillers, disintegrants, diluents, lubricants, pH buffering agents, or conventional adjuvants such as muramyl dipeptides, avridine, aluminium hydroxide, oils, saponins, block copolymers and other substances known in the art.

To immunize a subject, an antigen or gene vector can be administered parenterally, usually by intramuscular injection in an appropriate vehicle, but optionally by the subcutaneous route, by intravenous injection or by intradermal or intranasal delivery. In the case of immunization of fish, the typical routes of administration are by injection into the peritoneal cavity, orally in feed, or by immersion in sea water or fresh water. Consequently it is preferred to administer the amino acid sequences and nucleic acid sequences of the invention in the form of oral or injectable formulations, or as a liquid (for instance a liquid emulsion or emulsifiable concentrate) to be added to a water tank or bath where the fish are held.

The effective dosage may vary depending on the size and species of the subject, and according to the mode of administration. The optimal dosage can be determined through trial and error by an aquaculture specialist or veterinarian. Typically, a single dose of antigen will be in the range of from about 0.01 to 1000 μg per kg body weight, preferably 0.5 to 500 μg per kg, more preferably 0.1 to 100 μg per kg. For DNA vaccines, a minimum dosage of 10 pg up to dosages of 1000 pg of plasmid per animal should be sufficient for suitable expression of the antigen in vivo.

The novel antigens disclosed as part of the present invention are also useful in screening for antibodies to pathogenic proteins. The invention additionally includes diagnostic uses of these antigens, for instance in the preparation of a diagnostic kit, useful for testing animals for the presence of disease-causing organisms.

It is also contemplated that antibodies raised against the purified antigens of the invention can have both diagnostic and therapeutic applications in disease management. Both polyclonal antibodies and monoclonal antibodies may be useful in this respect. Sandwich assays and ELISA may be mentioned as specific examples of diagnostic assays.

EXAMPLES

Example 1

Efficacy of nucleic acid vaccines comprising *P. salmonis* antigen sequences

Coho salmon parr (*Oncorhynchus kisutch*) less than 6 months old and of average weight 5.4 grams were obtained from a disease free stock and were acclimatised to water at a temperature of 9±1° C., flowing at a rate of 2.5 L/min. Stocking densities were maintained at <20 kg/$m^3$, and the fish were fed a commercial pelleted diet at a daily rate of 1.5% body weight. The weight of fish in all groups was recorded prior to each vaccination and at the end of the trial. Any behavioural changes in the fish were also noted on a daily basis.

Coho salmon are particularly susceptible to infection with *P. salmonis*.

TABLE 1 sets out the experimental design:

| Group | Size | Treatment | Dose | Route |
|---|---|---|---|---|
| 1 | 110 | pUK blank | 25 μg | i.m. |
| 2 | 110 | pUK-Psclone51A | 25 μg | i.m. |
| 3 | 110 | pUK-Pshsp60 | 25 μg | i.m. |
| 4 | 110 | pUK-Ps17kD | 25 μg | i.m. |
| 5 | 110 | *P. salmonis*/oil | 0.1 ml | i.p. |
| 6 | 110 | PBS | 0.1 ml | i.m. |

The treatments were administered to randomly allocated groups of fish anaesthetized with 50 mg/L benzocaine, by single injection via the intramuscular (i.m.) route or intraperitoneal (i.p.) route.

pUK is an expression vector backbone which was not expected to induce any protection against SRS. pUK-psclone51A is a NAV construct carrying the entire ORF of Psclone51A. pUK-PsHSP60 is a NAV construct carrying the entire ORF of the *P. salmonis* hsp60 gene. pUK-Ps17kD is a NAV construct carrying the entire ORF of the *P. salmonis* p10.6 gene. The positive control group 4 was injected with a preparation of inactivated *P. salmonis* (strain LF89). This preparation is known to elicit protection against SRS, but is too expensive to produce on a commercial scale.

Following immunisation the fish were returned to holding tanks and kept there for 600 degree days before challenge. At this time fish from each treatment group were randomly divided into challenge tanks and control tanks. Treated fish were challenged by intraperitoneal injection with 0.1 ml containing approximately $10^{3.5}$ $TCID_{50}$ of cultured *P. salmonis*. Fish in each tank were monitored daily for mortality. Each mortality event was investigated for evidence of *P. salmonis* infection (by PCR).

Example 2

Immunogenicity of Antigens

Hsp60, Hsp70 and p10.6 nucleic acid sequences were inserted into a conventional expression vector. The recombinant proteins expressed in *E. coli* were purified and injected into mice in conjunction with an adjuvant. 40 days later, the mice were sacrificed and tested by ELISA for production of antibodies specific to the injected antigens. In every case, a specific immune response had been mounted to the antigen. A similar result was obtained when a plasmid NAV construct carrying the hsp70 gene was injected into mice.

These data provide solid evidence that the recombinant proteins Hsp60, Hsp70 and p10.6 are highly immunogenic, and are likely to be capable of inducing an immune response in fish, specifically targeting *P. salmonis* and thereby preventing development of SRS.

What is claimed is:

1. An isolated nucleic acid sequence comprising SEQ ID NO: 33.

2. The isolated nuclei acid sequence of claim 1 whereby said isolated nucleic acid sequence is isolated from *Piscirickettsia salmonis* type strain LF-89.

3. An isolated nucleic acid sequence having at least 80% homology the sequence set forth in to SEQ ID NO: 33, whereby said isolated nuclei acid sequence can detect *Piscirickettsia salmonis* DNA by stringent hybridization conditions, wherein said stringent conditions comprise 1X SSC, 0.1% SDS at 55° C.

4. A DNA expression vector comprising a nucleic acid of claim 1.

5. An isolated nucleic acid sequence encoding the amino acid sequence set forth in SEQ ID NO: 34.

6. An isolated polynucleotide fully complementary to the nucleic acid sequence of claim 1.

7. A diagnostic test kit for detecting *Piscirickettsia salmonis* DNS comprising an isolated polynucleotide of claim 6.

8. An isolated polynucleotide fully complementary to the nucleic acid sequence of claim 3.

* * * * *